United States Patent [19]
Tobe et al.

[11] Patent Number: 6,020,958
[45] Date of Patent: Feb. 1, 2000

[54] ATOMIC ABSORPTION SPECTROPHOTOMETER

[75] Inventors: Hayato Tobe, Mito; Kazuo Moriya, Hitachinaka; Hiromi Yamashita, Ishioka; Yasushi Terui, Hitachinaka, all of Japan

[73] Assignee: Hitachi, Ltd., Tokyo, Japan

[21] Appl. No.: 09/238,318

[22] Filed: Jan. 28, 1999

[30] Foreign Application Priority Data

Jan. 30, 1998 [JP] Japan ................................. 10-018527

[51] Int. Cl.⁷ ................................................. G01N 21/74
[52] U.S. Cl. ............................................................ 356/312
[58] Field of Search ................................... 356/319, 312

[56] References Cited

U.S. PATENT DOCUMENTS 4,890,919   1/1990   Tsukada et al. ......................... 356/312

FOREIGN PATENT DOCUMENTS 2259450A   10/1990   Japan .
658871A    3/1994    Japan .

*Primary Examiner*—F. L. Evans
*Attorney, Agent, or Firm*—Kenyon & Kenyon

[57] ABSTRACT

An atomic absorption spectrophotometer possessing an electrical heating unit which includes a graphite tube for atomizing a sample by heating the sample; a light emitting unit for emitting measuring light and irradiating the atomized sample with the measuring light; a spectroscope unit for diffracting the measuring light passing the electrical heating unit and selecting the required wavelength component; a detection unit for detecting the quantity of the required wavelength component selected by the spectroscope unit; an input unit to input at least one of the wavelengths of the required wavelength component and the required heating temperature of the electrical heating unit; and a control unit for controlling the above units, which comprises a shading device provided at the propagation axis of the measuring light between the electrical heating unit and the detection unit, and which possesses a light transmitting unit, for restricting the quantity of the measuring light passing the electrical heating unit, with the area of the light transmitting unit being changeable; and wherein the area of the light transmitting unit in the shading device is changed according to the set measurement conditions.

13 Claims, 7 Drawing Sheets

| SLIT NO. | WIDTH | LENGTH |
|---|---|---|
| 1 | 0.14 mm | 5 mm |
| 2 | 0.14 mm | 2 mm |
| 3 | 0.28 mm | 5 mm |
| 4 | 0.28 mm | 2 mm |
| 5 | 0.94 mm | 5 mm |
| 6 | 0.94 mm | 2 mm |
|  |  |  |
| 7 | 0.14 mm | 5 mm |
| 8 | 0.14 mm | 2 mm |
| 9 | 0.28 mm | 5 mm |
| 10 | 0.28 mm | 2 mm |
| 11 | 0.94 mm | 5 mm |
| 12 | 0.94 mm | 2 mm |

ATOMIC ABSORPTION SPECTROPHOTOMETER

BACKGROUND OF THE INVENTION

The present invention relates to an atomic absorption spectrophotometer using a graphite atomizer furnace method, which analyzes a metal element by heating a sample to be atomized and performing an atomic absorption spectrophotometry, and especially to an atomic absorption spectrophotometer using the graphite atomizer furnace method, by which the analytical accuracy is greatly improved.

FIG. 1 shows a schematic composition of a general atomic absorption spectrophotometer using the graphite atomizer furnace method.

As disclosed in Japan Patent Application Laid-Open Hei 2-259450 or Japan Patent Application Laid-Open Hei 6-58871, a sample 10 to be measured is placed in a graphite tube 2 provided in a graphite atomizer furnace 1, and is atomized by passing current through the graphite tube 2. A light source 3 with a diameter of 3 mm is generally used, and it emits a measuring light 4, including wavelength components of a wavelength range wider than 190–900 nm. The emitted measuring light 4 is converged by a convergence mirror 12, and the image of the emitted measuring light 4 is formed at the central position of the graphite tube 2. In the graphite tube 2, the atomic absorption of the measuring light 4 is caused by the sample 10, and the measuring light 4 which has received the atomic absorption is again converged by a convergence mirror 13 after passing though the graphite tube 2. The image of the converged measuring light 4 is formed at the position of an input slit in an input slit control unit 5. The formed image of the measuring light 4 is controlled by the input slit, and it is led to a spectrophotometer 6.

FIG. 2 illustrates a method of image formation for the measuring light 4 at the input slit. Numeral 20 indicates the input slit, and the quantity of the transmitted measuring light 4 is adjusted by changing the width of the input slit 20. The image 41 is the formed image of the measuring light 4, and its diameter is about 3 mm. The measuring light 4 emitted from the light source 3 has a strong rectilinear propagation property, and its image formed at the input slit 20, has almost the same diameter (3 mm) as that of the light source 3. Strictly speaking, it is the diameter of the image formed by the component of a reference wavelength predetermined as 250 nm. The diameters of the images of other wavelength components are not precisely 3 mm, and these images somewhat blur at the input slit 20. However, the diameter of these blurring images is at most 5 mm. Thus, the length of the input slit 20 is set to 5 mm in order not to decrease the quantity of the measuring light 4, which can pass through the input slit 20.

In the spectrophotometer 6, the measuring light 4 which has passed through the input slit 20 is diffracted, and the component of the required measuring wavelength is output to an output slit in an output slit control unit 11, and further led to a detector 8. The detector 8 converts the illuminance of the detected light to an electrical signal, and outputs the electrical signal to a central processing unit 7. The central processing unit 7 executes the temperature control of the graphite atomizer furnace 1, the current control for the light source 3, the input and output slit control units 5 and 11, and the selecting of the required measuring wavelength component. An input unit 9 sets the heating temperature of the graphite tube 2 when atomizing the sample 10, the required wavelength of the measuring light 4, and the value of current flowing in the light source 3.

In the above atomic absorption spectrophotometer using the graphite atomizer furnace method, since the graphite tube 2 is heated in the measuring operation, the graphite tube 2 itself emit light. Accordingly, the light emitted from the graphite tube 2 is input to the input slit 20 in addition to the measuring light 4. The light emitted from the graphite tube 2 becomes a background component disturbing the atomic absorption spectroscope measurement, and degrades the analytical accuracy of the atomic absorption spectrophotometry.

Therefore, in the conventional atomic absorption spectrophotometry, the background component has been removed by placing a shading plate before the input slit 20 to restrict the light emitted from the graphite tube 2.

However, in the above conventional composition in which the shading plate is additionally placed and fixed, since the measuring light 4 is also restricted by the shading plate at the same time the light emitted from the graphite tube 2 is restricted, the quantity of the measuring light 4 is decreased, which degrades the S/N ratio in the atomic absorption spectrophotometry.

Particularly, in measurements conducted under a low emission strength in the graphite tube 2—that is, measurements using the measuring light 4 with a short wavelength, or measurements with a low heating temperature for the heated graphite tube 2 when atomizing the sample 10, notwithstanding it is almost unnecessary to restrict the light emitted from the graphite tube 2—the light flux input to a detector is decreased by placing the shading plate, which largely degrades the analytical accuracy of the measurement.

SUMMARY OF THE INVENTION

An object of the present invention is to provide an atomic absorption spectrophotometer using a graphite atomizer furnace method, which is capable of improving the analytical accuracy by adequately removing the effects of the light emitted from a heated graphite tube without using an additional shading plate.

To attain the above object, the present invention provides an atomic absorption spectrophotometer possessing an electrical heating means which includes a graphite tube for atomizing a sample by heating the sample, a light emitting means for emitting measuring light and irradiating the atomized sample with the measuring light, a spectroscope means for diffracting the measuring light which has passed through the electrical heating means and selecting the required wavelength component, a detection means for detecting the quantity of the required wavelength component selected by the spectroscope means, an input means to input at least one of the wavelengths of the required wavelength components and the required heating temperature of the electrical heating means, and a control means for controlling the above means, the atomic absorption spectrophotometer comprising:

a shading device provided at the propagation axis of the measuring light between the electrical heating means and the detection means, which possesses a light transmitting means, for restricting the quantity of the measuring light which has passed through the electrical heating means, the area of the light transmitting means being changeable;

wherein the area of the light transmitting means in the shading device is changed according to the required measurement conditions.

Moreover, in the above atomic absorption spectrophotometer, the control means includes a memory for memorizing at least two predetermined wavelength regions with respect to the wavelength of the measuring light, and a comparison means for comparing the wavelength of the required wavelength component input from the input means with each of the predetermined wavelength regions;

wherein the light transmitting means includes a plurality of holes with different areas, and the control means selects one of the plurality of holes according to the comparison result executed by the comparison means to set the selected hole at the propagation axis of the measuring light.

Furthermore, in the above atomic absorption spectrophotometer, the control means includes a memory for memorizing one or more predetermined wavelength regions for wavelength components of the measuring light and one or more predetermined heating temperature regions with respect to the heating temperature of the electrical heating means, and a comparison means for comparing the required wavelength component input from the input means with each of the predetermined wavelength regions, and for comparing the required heating temperature also input from the input means with each of the predetermined heating temperature regions;

wherein the light transmitting means includes a plurality of holes with different areas, and the control means selects one of the plurality of holes according to the comparison results executed by the comparison means to set the selected hole at the propagation axis of the measuring light.

Additionally, in the above atomic absorption spectrophotometer, the predetermined wavelength component regions are a wavelength region of not less than 350 nm and a wavelength region of less than 350 nm.

Also, in the above atomic absorption spectrophotometer, the predetermined heating temperature regions are a temperature region of not less than 2000° C. and a temperature region of less than 2000° C.

Further, in the above atomic absorption spectrophotometer, the light transmitting means includes a plurality of slits with different areas, and the control means selects one of the plurality of slits according to the required wavelength component to set the selected slit at the propagation axis of the measuring light.

On top of that, in the above atomic absorption spectrophotometer, each of the plurality of slits is a rectangular slit with a different length and width, and the plurality of slits includes a rectangular slit with a length shorter than the diameter of an image of the measuring light, which is formed at the shading device, and another rectangular slit with a length longer than the diameter of the image of the measuring light.

Further still, in the above atomic absorption spectrophotometer, the shortest length of the rectangular slit is 2 mm, and the longest length of the rectangular slit is 5 mm.

Moreover, in the above atomic absorption spectrophotometer, the plurality of slits are provided in two sets of slits, and the respective two sets of slits are placed at the propagation axis of the measuring light before and after the spectroscope means.

Also, in the above atomic absorption spectrophotometer, the two sets of slits are formed in the same member.

Furthermore, in the above atomic absorption spectrophotometer, the member including the two sets of slits is rotatably attached, and a pair of slits of the same size, each slit in the pair being formed in each of the two sets, is selected and set by rotating the member.

And further, in the above atomic absorption spectrophotometer, the control means also includes a light transmitting area adjusting means for optimally adjusting the area of the light transmitting means in the shading device in accordance with the required measurement conditions.

DETAILED DESCRIPTION OF THE EMBODIMENTS

Hereafter, details of embodiments will be explained with reference to the FIGS. 3–9.

Figure 3:
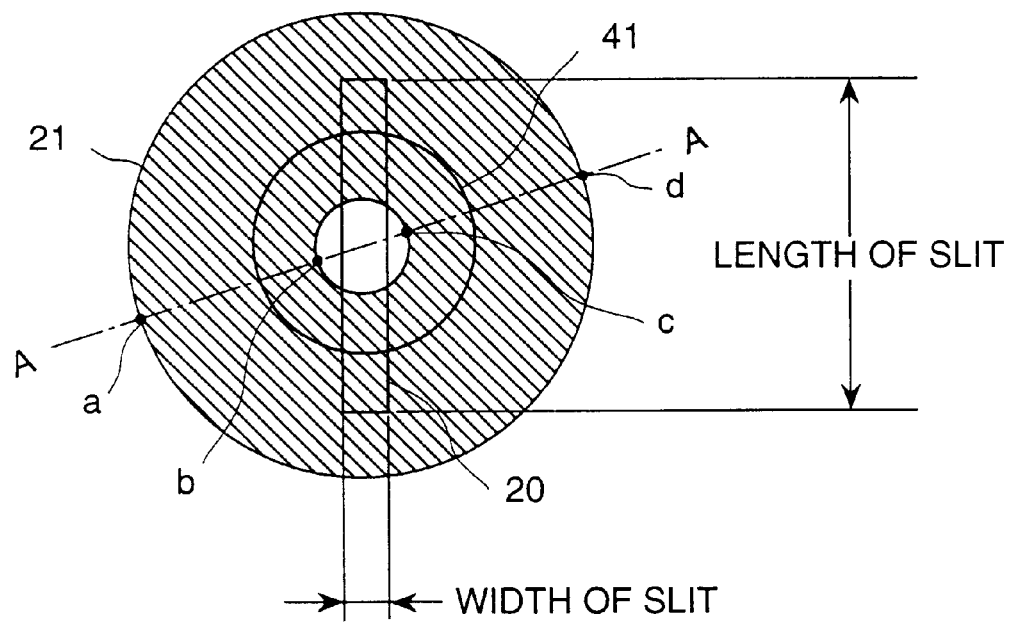
FIG. 3 is a diagram showing the relationship between the image of the measuring light and an image of light emitted from a graphite tube, both of which are formed at the input slit.

FIG. 3 is a diagram showing the relationship between the image of measuring light and an image of light emitted from the graphite tube, both of which are formed at an input slit in an input slit control unit. In this figure, numerals 20, 41, and 21 indicate the input slit, the image of measuring light 4, which is formed at the input slit 20, and the image of light in the visible region, emitted from the inside surface of the graphite tube 2, which is also formed at the input slit 20, respectively.

The light converged into the image 21 is emitted from the inside surface of the heated graphite tube 2, and since the graphite tube 2 has a definite length in the propagation axis direction of the measuring light 4, and the light emitted from the inside surface of the graphite tube 2 is reflected by the inside surface, the image 21 shows a blurring annular image. Moreover, the illuminance distribution is not uniform in the image 21, and it changes in the radial direction.

Figure 4:
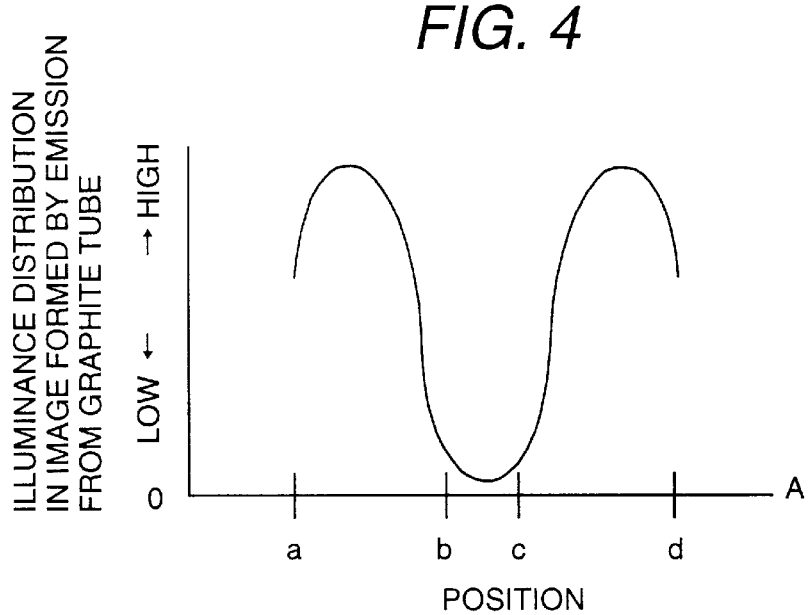
FIG. 4 shows the illuminance distribution in the image of the light emitted from the graphite tube, which is formed at the input slit.

FIG. 4 shows an illuminance distribution in the line A—A in the image 21 of the light emitted from the graphite tube, which is formed at the input slit 20. The region of (a-b) and the region of (c-d) in FIG. 4 correspond to the annular image 21, and the region of (b-c) corresponds to the central opening part of the annular image 21. As seen in FIG. 4, in the illuminance distribution of the image 21, the illuminance is lowest in the central opening part of the annular image 21. Furthermore, it increases toward the outer periphery of the image 21, and reaches the maximum value at an intermediate position in the annular region of the image 21. Afterward, it gradually decreases. The numerical values in the illuminance distribution depend on measurement conditions such as the wavelength of the measuring light 4, the heating temperature of the graphite tube 2, and so on. However, the relative shape of the illuminance distribution of the image 21 is almost the same as that shown in FIG. 4 under any measurement condition.

The inner and outer diameter values of the image 21 formed by the light emitted from the graphite tube 2 are much larger than the diameter of the image 41 of the measuring light 4, and the overlapping part of the images 21 and 41 has a wide area.

In a conventional atomic absorption spectrophotometer, since an input slit in which the length is fixed at about 5 mm is used as the input slit 20, the image 21 adversely affects the image 41 as a background component. This adverse effect becomes more noticeable with the increase in the wavelength of the measuring light 4 and the heating temperature of the graphite tube 2 in the measuring conditions.

Figure 5:
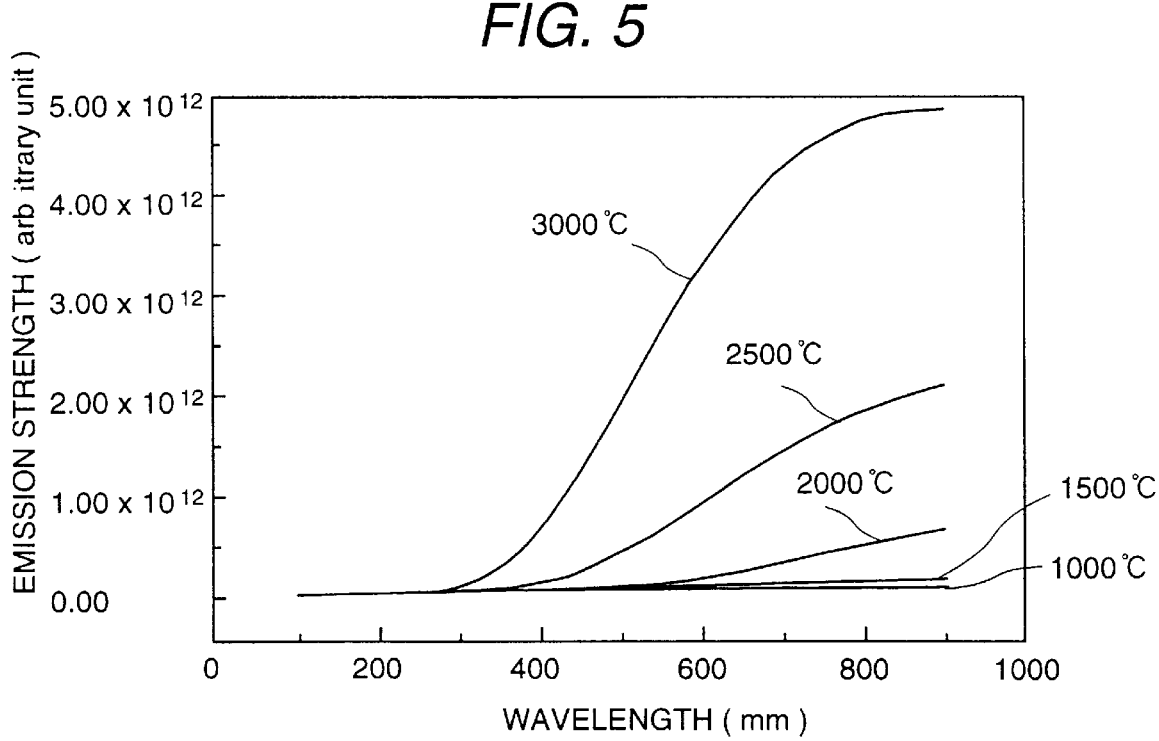
FIG. 5 shows the relationship between the emission strength of the light emitted from the graphite tube and the wavelength of the measuring light when changing the heating temperature of the graphite tube.

FIG. 5 shows the relationship between the emission strength of the light emitted from the graphite tube 2 and the wavelength of the emitted light while changing the heating temperature of the graphite tube 2. The curves shown in FIG. 5 are obtained by calculating a theoretical equation formulated to express the relationship between the emission strength of the light emitted from the graphite tube 2 and the wavelength of the emitted light. In the wavelength range of 100 nm–900 nm in this figure, it is seen that although the emission strength of the light emitted from the graphite tube 2 is very low in the short wavelength range, the emission strength increases with the increase of the wavelength. The higher the heating temperature of the graphite tube 2 is, the more noticeable this tendency is. That is, up to a heating temperature of 2000° C., the increase in the emission strength is small over the whole range of wavelengths. However, over a heating temperature of 2000° C., the emission strength rapidly increase in the range of 300 nm–400 nm.

If the quantity of the light emitted from the graphite tube 2 is less than that of the measuring light 4, the light emitted from the graphite tube 2 does not practically affect the measurement. In other words, the light from the graphite tube 2 for which the emission strength is less than $0.50 \times 10^{12}$ (arb. unit) can be sufficiently corrected for as a background component. Under the measurement conditions of the above emission strength grade, it is not necessary to shade the light from the graphite tube 2.

Thus, in the present invention, on the basis of the relationship among the emission strength of the light emitted from the inside surface of the graphite tube 2, the wavelength of the measuring light 4, and the heating temperature of the graphite tube 2, a plurality of input slits 20 with different length are provided, and one of the plurality of input slits 20 is selected according to the emission strength of the light from the graphite tube 2.

Table 1 shows the relationship between the quantity of the light from the graphite tube 2, which is transmitted through the input slit 20, and the length of the input slit 20.

TABLE 1

| | The length of slit (the width: 0.94 mm) | | | |
| --- | --- | --- | --- | --- |
| | 1 mm | 2 mm | 3 mm | 5 mm |
| Relative quantity A of transmitted light emitted from graphite tube (1.00 at 2 mm) | 0.41 | 1.00 | 1.62 | more than 10 (beyond the limit of measurement) |
| Ratio: A/quantity of measuring light (%) | 100 | 91 | 104 | more than 410 (beyond the limit of measurement) |

Measurement conditions: wavelength; 766.5 nm
heating temp.; 2800° C.

The values described in Table 1 are obtained from measured data under measurement conditions in which the wavelength of the measuring light 4 is 766.5 nm and the heating temperature for the graphite tube 2 is 2800° C. It is estimated at 2800° C. in FIG. 5 that the emission strength of the light emitted from the graphite tube 2 is a high value of about $3.00 \times 10^{12}$ (arbitrary unit).

As shown in Table 1, if the length of the input slit 20 is 5 mm, the quantity of the light emitted from the graphite tube 2 which has been transmitted through the input slit is more than 10 times of that of the measuring light 4, and this value is far beyond the measurement limit for the atomic absorption spetrophotometry. Accordingly, it is preferable to set the length of the input slit to less than 3 mm. Moreover, it is known from the values of the ratio shown in Table 1: the quantity of the transmitted light emitted from the graphite tube 2 to the quantity of the transmitted measuring light that the effect due to the light emitted from the graphite tube 2 becomes minimal at a length of 2 mm.

Figure 1:
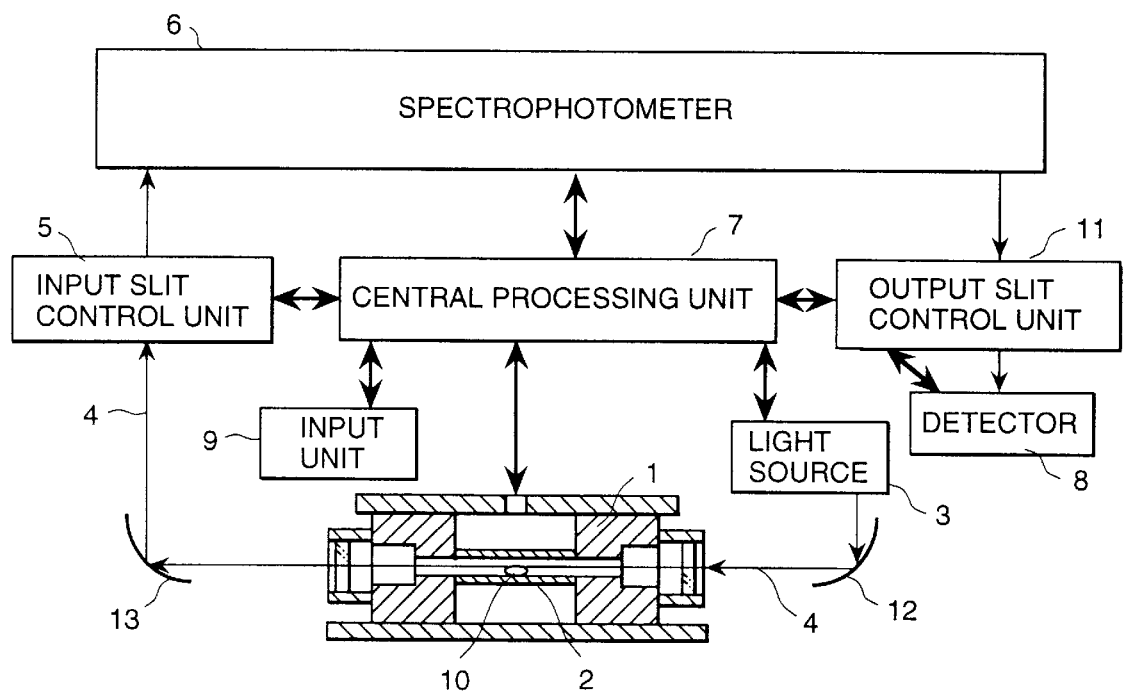
FIG. 1 is a diagram showing a schematic composition of a general atomic absorption spectrophotometer.
Figure 2:
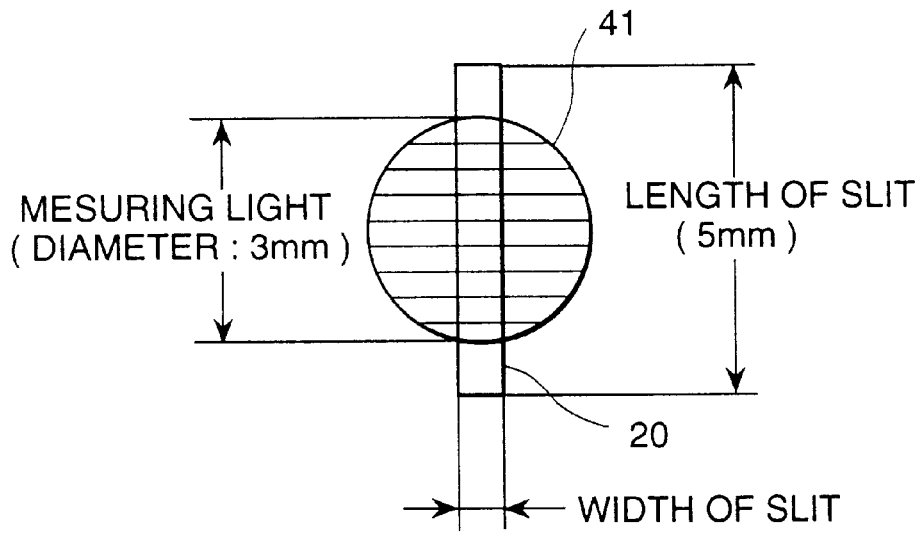
FIG. 2 shows an example of an image of measuring light, which is formed at an input slit plate.

Therefore, in the present invention, on the basis of the results shown in FIG. 2, the reference wavelength λ of the measuring light 4 and the reference heating temperature T for the graphite tube 2 are set to 350 nm and 2800° C., respectively. Furthermore, on the basis of the results shown in Table 1, two kinds of slits of the lengths 2 mm and 5 mm are provided as the input slit 20. In executing the measurement, it is determined to which regions concerning the above reference values the set wavelength and the set heating temperature in the measurement conditions correspond, respectively. And then, if the measurement conditions are such that the effect of the light emitted from the graphite tube 2 is not negligible, the 2 mm slit is used as the input slit 20, otherwise, the 5 mm slit is used as the input slit 20. In accordance with the above-explained slit selecting method, it is possible to optimally shade the light emitted from the graphite tube 20. That is, if the measurement conditions are such that the light from the graphite tube 2 only slightly affects the measurement, a larger quantity of the measurement light 4 can be transmitted through the input slit 20. Also, two kinds of output slits are also provided corresponding to the two kinds of input slits. According to this embodiment, highly accurate measurement in atomic absorption spetrophotometry becomes possible.

Figure 6:
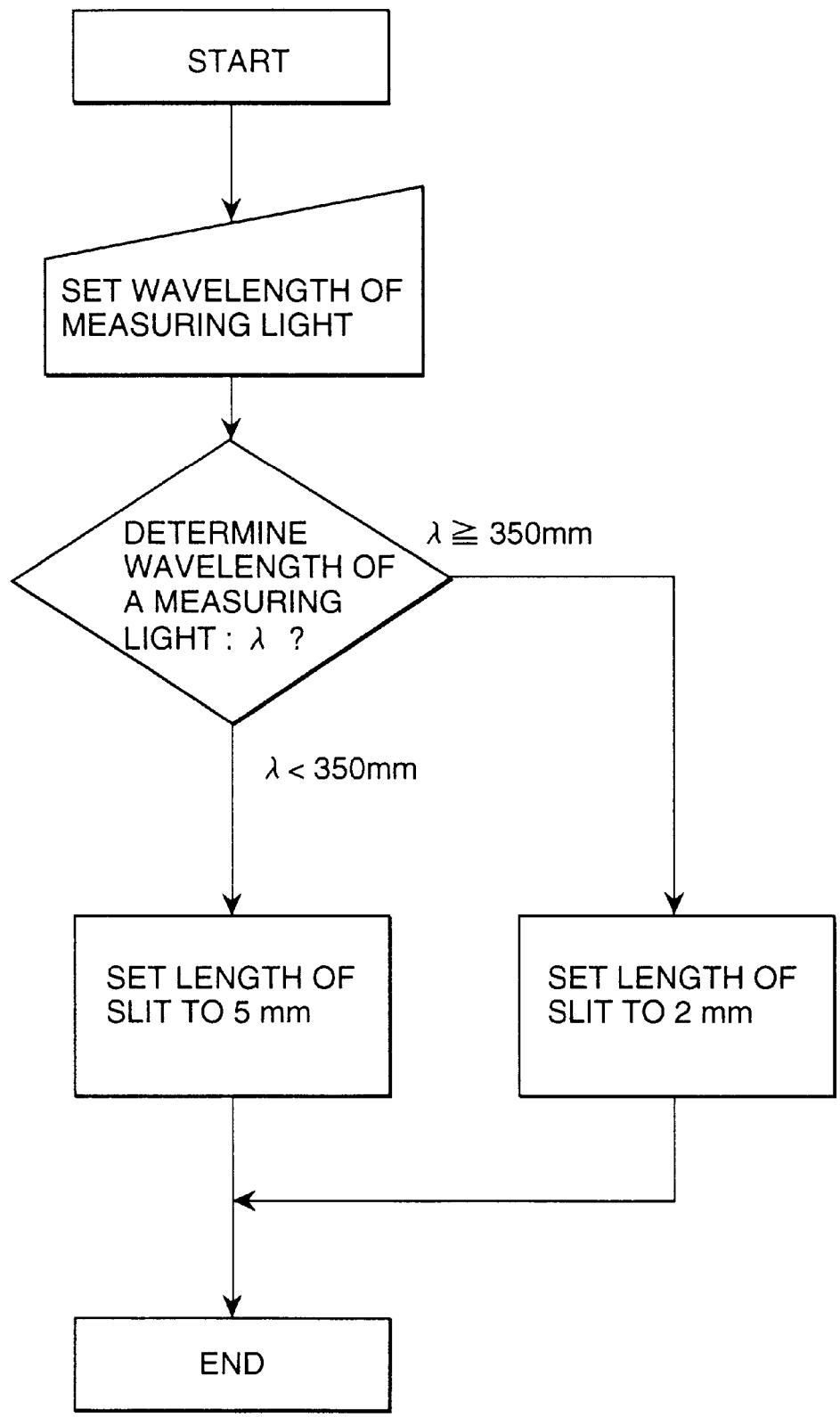
FIG. 6 is a flow chart for selecting an optimal slit under a predetermined reference value for a required wavelength component of the measuring light.
Figure 7:
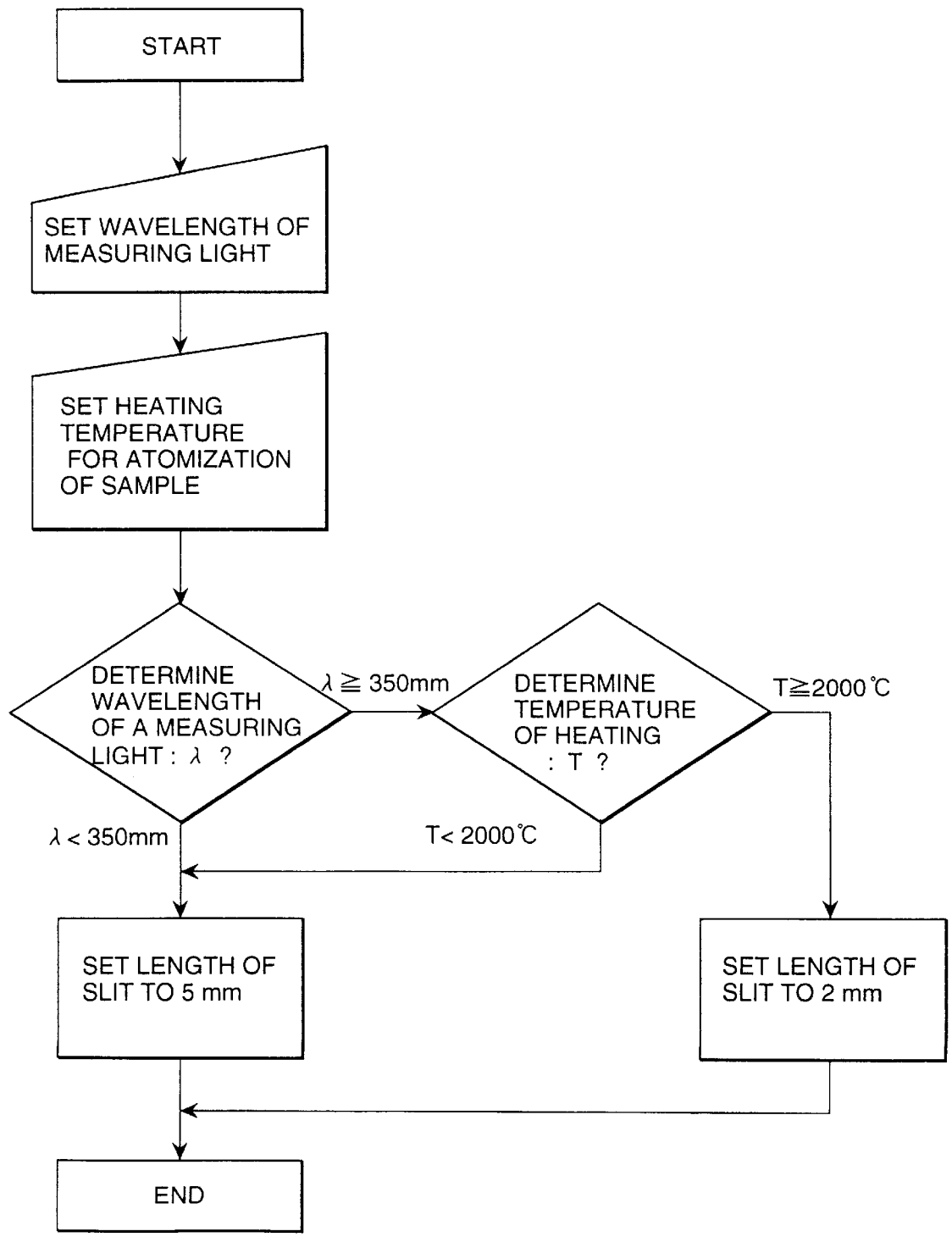
FIG. 7 is a flow chart for selecting an optimal slit under two predetermined reference values for a required wavelength component of the measuring light and for the heating temperature of the graphite tube.

FIGS. 6 and 7 show examples of flow charts for selecting one of the two kinds of slits before starting the measurement.

FIG. 6 is a flow chart for the procedures of selecting a slit when the reference wavelength of the measuring light 4 is used as the reference value for determining the measurement conditions. The reference wavelength λ of 350 nm is stored in the memory (not shown in the figures) of the central processing unit 7 in advance by using the input unit 9.

To begin with, the value of the current to operate the light source 3 and the wavelength λ of the measuring light 4 are input from the input unit 9 before the measurement.

Next, the input wavelength is compared with the reference wavelength stored in the memory by the central processing unit 7. If the input wavelength is less than 350 nm, since it can be determined that the effect of the light emitted from the graphite tube 2 is slight, the 5 mm slit is selected for the input slit 20. Also, the slit corresponding to the slit selected for the input slit 20 is further set to the output slit.

On the other hand, if the input wavelength is not less than 350 nm, since it can be determined that the effect of the light emitted from the graphite tube 2 is not negligible, the 2 mm slit is selected for the input slit 20. Also, the slit corresponding to the slit selected for the input slit 20 is further set to the output slit. The setting of the selected slit to each of the input slit 20 and the output slit is performed by of the length the input slit control unit 5 and the output slit control unit 11, respectively.

FIG. 7 is a flow chart for the procedures of selecting an optimal slit when the reference heating temperature for the graphite tube 2 is further used as an additional reference value for determining the measurement conditions. In this procedure, the reference wavelength λ of 350 nm and the reference heating temperature of 2000° C. are stored in the memory of the central processing unit 7 in advance by using the input unit 9.

To begin with, the value of the current to operate the light source 3, the required wavelength λ of the measuring light 4, and the required heating temperature T set for atomizing the sample are input from the input unit 9 before starting the measurement.

Next, the input wavelength is compared with the reference wavelength stored in the memory of the central processing unit 7. If the input wavelength is less than 350 nm, since it can be determined that the effect of the light emitted from the graphite tube 2 is slight, the 5 m slit is selected for the input slit 20. Also, the slit corresponding to the slit selected for the input slit 20 is set to the output slit.

On the other hand, if the input wavelength is not less than 350 nm, since the measurement may be affected by the light emitted from the graphite tube 2, the heating temperature set for atomizing the sample 10 is compared with the reference heating temperature stored in the memory. If the set heating temperature is less than 2000° C., since it can be determined that the effect of the light emitted from the graphite tube 2 is slight, the 5 mm slit is selected for the input slit 20. Also, the slit corresponding to the slit selected for the input slit 20 is further set to the output slit. Conversely, If the input heating temperature is not less than 2000° C., since it can be determined that the effect of the light emitted from the graphite tube 2 is not negligible, the 2 mm slit is selected for the input slit 20. Also, the slit corresponding to the slit selected for the input slit 20 is further set to the output slit.

After the optimal slit is selected, the central processing unit 7 sets the wavelength λ of the measuring light 4 to the spectrophotometer 6 as shown in FIG. 6 and FIG. 7, and further controls current to operate the light source 3. Afterward, the central processing unit 7 controls the temperature of the graphite atomizer furnace 1, and the sample 10 in the graphite tube 2 is atomized. Furthermore, the measuring light 4 which has received the atomic absorption of the atomized sample 10 and been restricted by the input slit control unit 5 is input to the spectrophotometer 6, and only the measuring light 4 of the set wavelength is led to the detector 8 via the output slit control unit 11. Subsequently, the detected quantity of the measuring light 4 is output to the central processing unit 7 from the detector 8. Finally, the central processing unit 7 calculates the quantity of the atomic absorption based on the input quantity of the measuring light 4, and the measurement of the atomic absorption is completed.

Figures 8A, 8B:
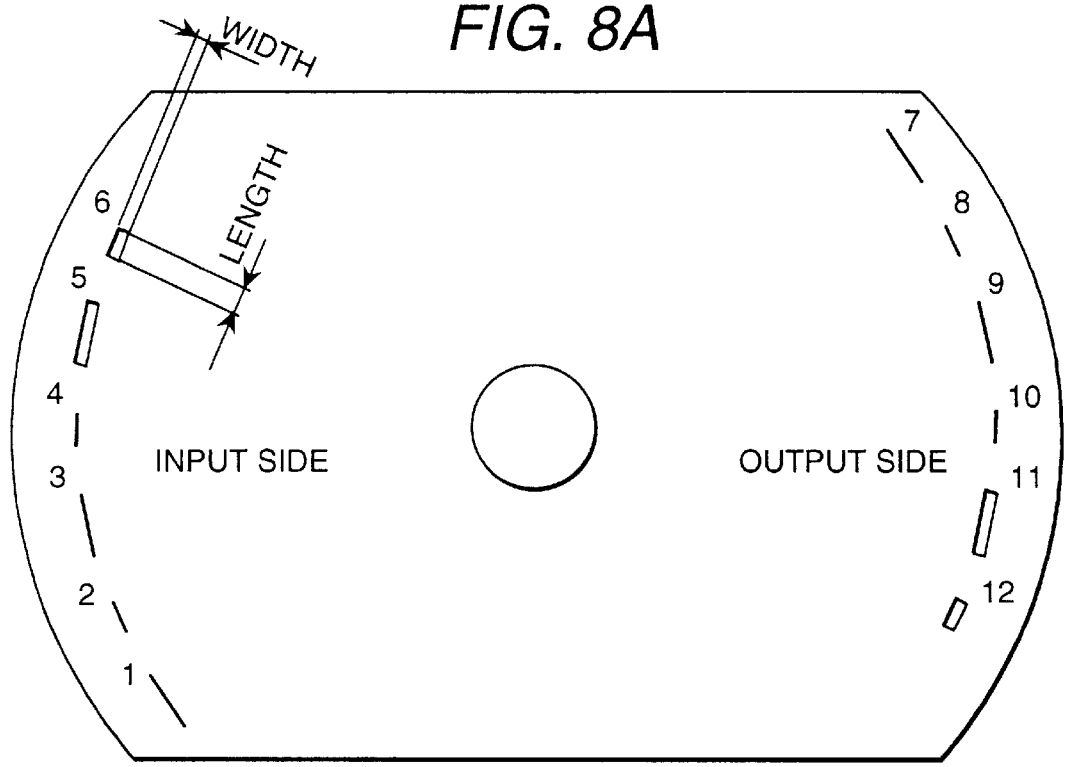
FIG. 8A and FIG. 8B are an example of a member in which two sets of slits are provided for input slits and output slits, respectively.

FIG. 8A and FIG. 8B are an example of a member in which two sets of slits are provided for the input slit control unit 14 and the output slit control unit 15, respectively.

In the example shown in FIGS. 8A and 8B, the set of input slits and the set of output slits are formed in the same member. Moreover, three different values with respect to the width are provided for each length; that is, for 2 mm and 5 mm, in both the sets of the input slits and the output slits. Furthermore, a pair of slits of the same size, each half of which exists in one of the set of input slits and the set of output slits is formed symmetrically with respect to the rotation axis of the member so that the setting of the input slit 20 in the input slit control unit 5 can be carried out at the same time of setting the output slit in the output slit control unit 11.

As explained above, in accordance with the present invention, the effects of the light emitted from the graphite tube 2 is estimated based on the set measurement conditions of the wavelength of the measuring light 4 and the heating temperature for the graphite tube 2, and an optimal size for the input slit and the output slit is selected to avoid the effect of the light emitted from the graphite tube 2. Thus, highly accurate measurement becomes possible without unnecessary deterioration in the measurement accuracy.

The reason why a plurality of slits of different widths is provided is for the purpose of taking the following countermeasures. That is, the resolution of the wavelength in the diffraction of light executed by the spectrophotometer 6 and the quantity of the measuring light 4 input to the spectrophotometer 6 depend on the width of the input slit 20. On the other hand, since the light source 3 emits a light beam with a bright line spectrum in the atomic absorption spectrophotometry, it is necessary to change the width of the input slit 20 according to either the presence of a line spectrum neighboring the absorption line spectrum of an element in the sample 10 or the quantity of the measuring light 4 which has passed through the input slit 20 and been input to the spectrophotometer 6. Thus, in this embodiment, if the line spectrum neighboring the absorption line spectrum exists, the width of the input slit is reduced. Otherwise, by increasing the width of the input slit, the quantity of the input measuring light 4 is increased.

In the above embodiments, although the optimal length value of 2 mm or 5 mm is determined for the length of the input and output slits, those values of 2 mm and 5 mm are predetermined depending on the diameter of the light source 3, the inner diameter of the graphite tube 2, the path from the input slit to the spectrophotometer 6, along which the measuring light 4 propagates, the path from the spectrophotometer 6 to the output slit, along which the measuring light 4 propagates, and so on. Actually, the length values of the slits are predetermined on the basis of calculational simulation or preliminary test measurement performed under the constraint that the quantity of the measuring light 4> the quantity of the light emitted from the graphite tube 2 after the input slit 20.

Figure 9:
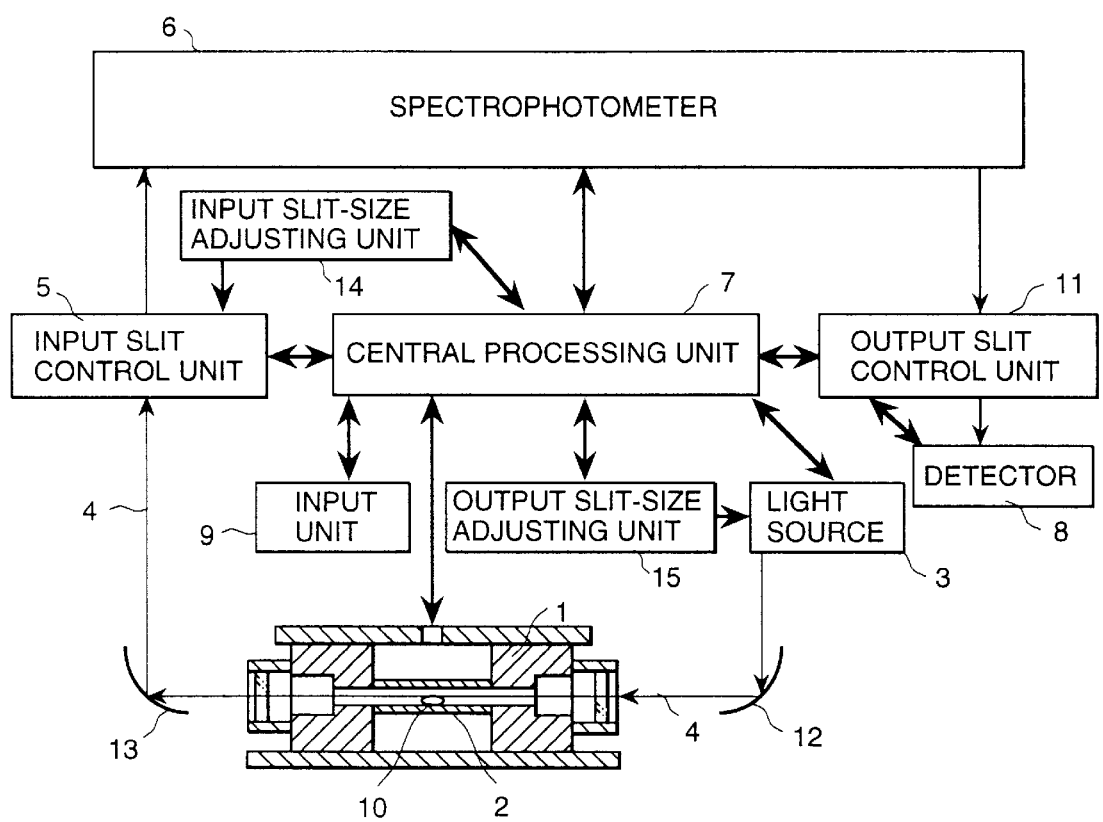
FIG. 9 is a diagram showing a schematic composition of an atomic absorption spectrophotometer of another embodiment according to the present invention.

FIG. 9 is a diagram showing a schematic composition of an atomic absorption spectrophotometer of another embodiment according to the present invention. In the above-explained embodiments, a plurality types of input and output slits with different length and/or width values are provided, and one pair of the plurality types of input and output slits which is optimal for the set measurement conditions is selected. On the other hand, in this embodiment, one slit is provided in each of the input slit control unit 5 and the output slit control unit 11, and the length and/or width of each slit is adjusted according to the set measurement conditions. In FIG. 9, numerals 14 and 15 indicate an input slit-size adjusting unit and an output slit-size adjusting unit, respectively. The control actions performed by the slit-size adjusting units 14 and 15 are explained below. First, the value of the current to operate the light source 3, the required wavelength of the measuring light 4, and the required heating temperature for atomization of the sample 10 are set from the input unit 6 before starting the measurements. Next, the graphite tube 2 is heated to the set heating temperature for atomization of the sample 10. Afterward, while the length of the input and output slits are changed by the input and output slit-size adjusting units 14 and 15, the quantity of the measuring light 4 and the quantity of the light emitted from the graphite tube 2 which have passed through the respective input and output slits are measured, and each value of the measured quantities is stored in the memory of the central processing unit 7. After the completion of the measurement, the central processing unit 7 calculates the ratio of the measured quantity of the light emitted from the graphite tube 2 to that of the measuring light 4 with respect to each set length of the input and output slits. Furthermore, the central processing unit 7 determines the length of the slits which minimizes the ratio, and stores the determined length in its memory. Afterward, the central processing unit 7 sends the value of the stored length to the input- and output slit-size adjusting units 14 and 15, and to each of the input and output slit control units 5 and 11. Each of the adjusting units 14 and 15 sends a control signal for adjusting the length of each slit according to the value sent from the central processing unit 7. Thus, the length of each slit-part is set to the optimal length by each of the input and output slit control units 5 and 11. According to this embodiment, since the optimal length of each slit can be set corresponding to the measurement conditions in every measurement, the SIN ratio is increased, and the measurement accuracy can be further improved.

In accordance with the present invention, the length of slits can be automatically set to the optimal value. Accordingly, in the short wavelength range, since the measuring light can be input to a spectrophotometer without an unnecessary restriction, it is possible to provide an atomic absorption spectrophotometer using a graphite atomizer furnace method, which can increase the S/N ratio, and further improve the measurement accuracy. Furthermore, in the long wavelength range, the atomic absorption spectrophotometer according to the present invention is remarkably effective even for measurements under the condition of a low heating temperature for atomization of a sample, as well as in the short wavelength range.

What is claimed is:

1. An atomic absorption spectrophotometer possessing an electrical heating means which includes a graphite tube for atomizing a sample by heating the sample, a light emitting means of emitting measuring light and irradiating said atomized sample with said measuring light, a spectroscope means for diffracting said measuring light passing said electrical heating means and selecting a required wavelength component, a detection means for detecting the quantity of said required wavelength component selected by said spectroscope means, an input means to input at least one of the wavelength of said required wavelength component and the required temperature of said electrical heating means, and a control means for controlling said above means, said atomic absorption spectrophotometer comprising:

a shading device which possesses a light transmitting means, and is provided at the propagation axis of said measuring light between said electrical heating means and said detection means, for restricting the quantity of said measuring light between said electrical heating means and said detection means, for restricting the quantity of said measuring light passing said electrical heating means, the area of said light transmitting means being changeable;

wherein the area of said light transmitting means in said shading device is changed according to the set measurement conditions.

2. An atomic absorption spectrophotometer according to claim 1, in which said control means includes a memory for recording at least two predetermined wavelength regions with respect to the wavelength of said measuring light, a comparison means for comparing the wavelength of said required wavelength component input from the input means with each of said predetermined wavelength regions;

wherein said light transmitting means includes a plurality of holes with different areas, and said control means selects one of said plurality of holes according to the comparison result executed by said comparison means to set said selected hole at the propagation axis of said measuring light.

3. An atomic absorption spectrophotometer according to claim 1, in which said control means includes a memory for recording one or more predetermined wavelength regions with respect to the wavelength of the measuring light and one or more predetermined heating temperature regions with respect to the heating temperature of said electrical heating means, a comparison means for comparing the wavelength of said required wavelength component input from said input means with each of said predetermined wavelength regions, and comparing said required heating temperature also input from said input means with each of said predetermined heating temperature regions;

wherein said light transmitting means includes a plurality of holes with different areas, and said control means selects one of said plurality of holes according to the comparison results executed by said comparison means to set said selected hole at the propagation axis of said measuring light.

4. An atomic absorption spectrophotometer according to claim 2, in which said predetermined wavelength component regions are a wavelength region of not less than 350 nm and a wavelength region of less than 350 nm.

5. An atomic absorption spectrophotometer according to claim 3, in which said predetermined heating temperature regions are a temperature region of not less than 2000° C. and a temperature region of less than 2000° C.

6. An atomic absorption spectrophotometer according to claim 1, in which said light transmitting means includes a plurality of slits with different areas, said control means selects one of said plurality of slits in accordance with said required wavelength component, and sets said selected slit at the propagation axis of said measuring light.

7. An atomic absorption spectrophotometer according to claim 6, in which each of said plurality of slits is a rectan gular slit with a different length and a different width, and where said plurality of slits include a rectangular slit with the length shorter than the diameter of an image of said measuring light, which is formed at said shading device, and another rectangular slit with the length longer than the diameter of said image of said measuring light.

8. An atomic absorption spectrophotometer according to claim 7, in which said shorter length of said rectangular slit is 2 mm, and said longer length of said rectangular slit is 5 mm.

9. An atomic absorption spectrophotometer according to claim 6, in which said plurality of slits is provided in two sets of slits, and said respective two sets of slits are placed at the propagation axis of said measuring light before and after said spectroscope means.

10. An absorption spectrophotometer according to claim 9, in which said two sets of slits are formed in the same member.

11. An atomic absorption spectrophotometer according to claim 10, in which said member in which said two sets of slits is formed is rotatably attached, and a pair of slits of the same size, each of which is formed in each of said two sets, is selected and set by rotating said member.

12. An atomic absorption spectrophotometer according to claim 1, which further includes a light transmitting area adjusting means for optimally adjusting the area of said light transmitting means in said shading device in accordance with said set measurement conditions.

13. An atomic absorption spectrophotometer according to claim 3, in which said predetermined wavelength component regions are a wavelength region of not less than 350 nm and a wavelength region of less than 350 nm.

* * * * *